(12) United States Patent
Suzuki et al.

(10) Patent No.: US 6,503,235 B2
(45) Date of Patent: Jan. 7, 2003

(54) DISPOSABLE PULL-ON UNDERGARMENT

(75) Inventors: Seiji Suzuki, Kagawa-ken (JP); Takaaki Shimada, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/901,412

(22) Filed: Jul. 9, 2001

(65) Prior Publication Data

US 2002/0010450 A1 Jan. 24, 2002

(30) Foreign Application Priority Data

Jul. 19, 2000 (JP) ........................................ 2000-218509

(51) Int. Cl.[7] .......................... A61F 13/15; A61F 13/20; A41B 9/00
(52) U.S. Cl. .............................. 604/385.11; 604/385.27; 604/385.28; 604/385.29; 604/396; 2/400; 2/401
(58) Field of Search ....................... 604/388.01, 385.11, 604/385.2, 385.21, 385.22, 385.23, 386, 393–396; 2/400–408

(56) References Cited

U.S. PATENT DOCUMENTS

| 2,435,945 | A | * | 2/1948 | Redmond |
| 3,000,381 | A | * | 9/1961 | Mulhole et al. |
| 4,205,679 | A | * | 6/1980 | Repke et al. ............... 604/394 |
| 4,630,320 | A | * | 12/1986 | Van Gompel |
| 5,182,815 | A | * | 2/1993 | Young .......................... 2/406 |

FOREIGN PATENT DOCUMENTS

| JP | 10-75980 | 3/1998 |
| JP | 10-99373 | 4/1998 |
| JP | 10-204704 | 8/1998 |

* cited by examiner

Primary Examiner—Dennis Ruhl
Assistant Examiner—K. M. Reichle
(74) Attorney, Agent, or Firm—Baker & Daniels

(57) ABSTRACT

A disposable pull-on undergarment having front and rear waist regions bonded together along longitudinally extending bonding zones to define a waist-hole and a pair of leg-holes. The respective bonding zones have an upper end lying most adjacent the waist-hole and a lower end lying most adjacent the leg-holes and extend from the upper ends toward the lower ends so that these bonding zones approach a longitudinal center line X of the undergarment.

3 Claims, 6 Drawing Sheets

DISPOSABLE PULL-ON UNDERGARMENT

BACKGROUND OF THE INVENTION

This invention relates to a disposable pull-on undergarment and more particularly to a pull-on undergarment such as a disposable pants-type diaper, training pants or incontinent pants.

Conventional disposable pull-on undergarments are composed of front and rear waist regions opposed to each other and a crotch region extending between these two waist regions. The front and rear waist regions are connected with each other at bonding zones that extend along transversely opposite side edge portions thereof so as to define a waist-hole and a pair of leg-holes. Such undergarments are disclosed, for example, in Japanese Patent Application Publication Nos. 1998-75980A, 1998-99373A and 1998-204704A. As is common in these undergarments, the respective bonding lines extend along transversely opposite sides of a wearer's waist.

To take off or remove a used undergarment from the wearer lying on his or her back, a helper for the wearer may tear open the undergarment along the bonding zones. The force required by the helper to tear open the used undergarment is exerted on the undergarment in a direction from side edges of the waist-hole toward a transversely middle zone of the undergarment in the crotch region.

In the case of the undergarments disclosed in the above Publications, the direction of the tearing force does not coincide with the direction of the bonding lines. Accordingly, although the force is exerted upon the bonding zones, it is not necessarily exerted on the bonding lines as the used undergarment is torn open and consequently there is an apprehension that the undergarment may not be smoothly torn open along the bonding lines.

SUMMARY OF THE INVENTION

It is an object of this invention to provide a disposable pull-on undergarment that is designed so that the undergarment can be smoothly torn open along the bonding lines.

According to this invention, there is provided a disposable pull-on undergarment having front and rear waist regions opposed to each other and a crotch region extending between these two waist regions wherein these front and rear waist regions are connected with each other at bonding zones that extend along transversely opposite side edge portions thereof so as to define a waist-hole and a pair of leg-holes.

According to this invention the bonding lines respectively have upper end portions lying adjacent the waist-hole and lower end portions lying adjacent the pair of leg-holes so that the bonding lines approach a longitudinal center line vertically extending across circumferential middle zones of the front and rear waist regions as the bonding lines extend from the upper end portions toward the lower end portions.

According to one embodiment of this invention, the bonding lines extend at an angle of 5~30° with respect to the longitudinal center line.

According to another embodiment of this invention, the undergarment comprises a liquid-pervious topsheet, a liquid-impervious backsheet and a liquid-absorbent panel disposed between these two sheets.

DETAILED DESCRIPTION OF THE PREFERRED EMBODIMENTS

Details of a disposable pull-on undergarment according to this invention will be more fully understood from the following description of a disposable pants-type diaper given hereunder with reference to the accompanying drawings.

Figure 1:
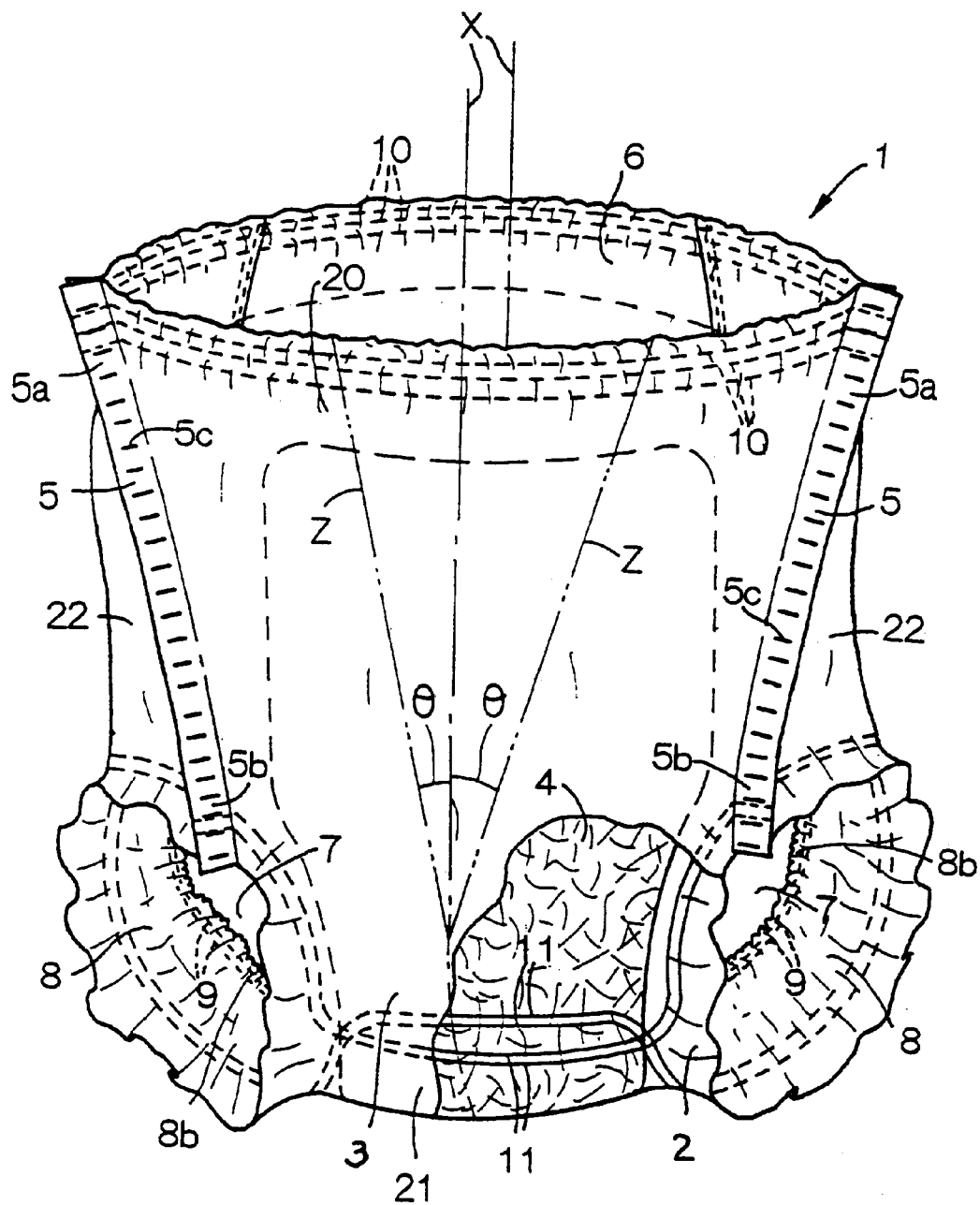
FIG. 1 is a perspective view showing a disposable diaper according to one embodiment of this invention as viewed from the side of a front waist region and partially broken away.
Figure 2:
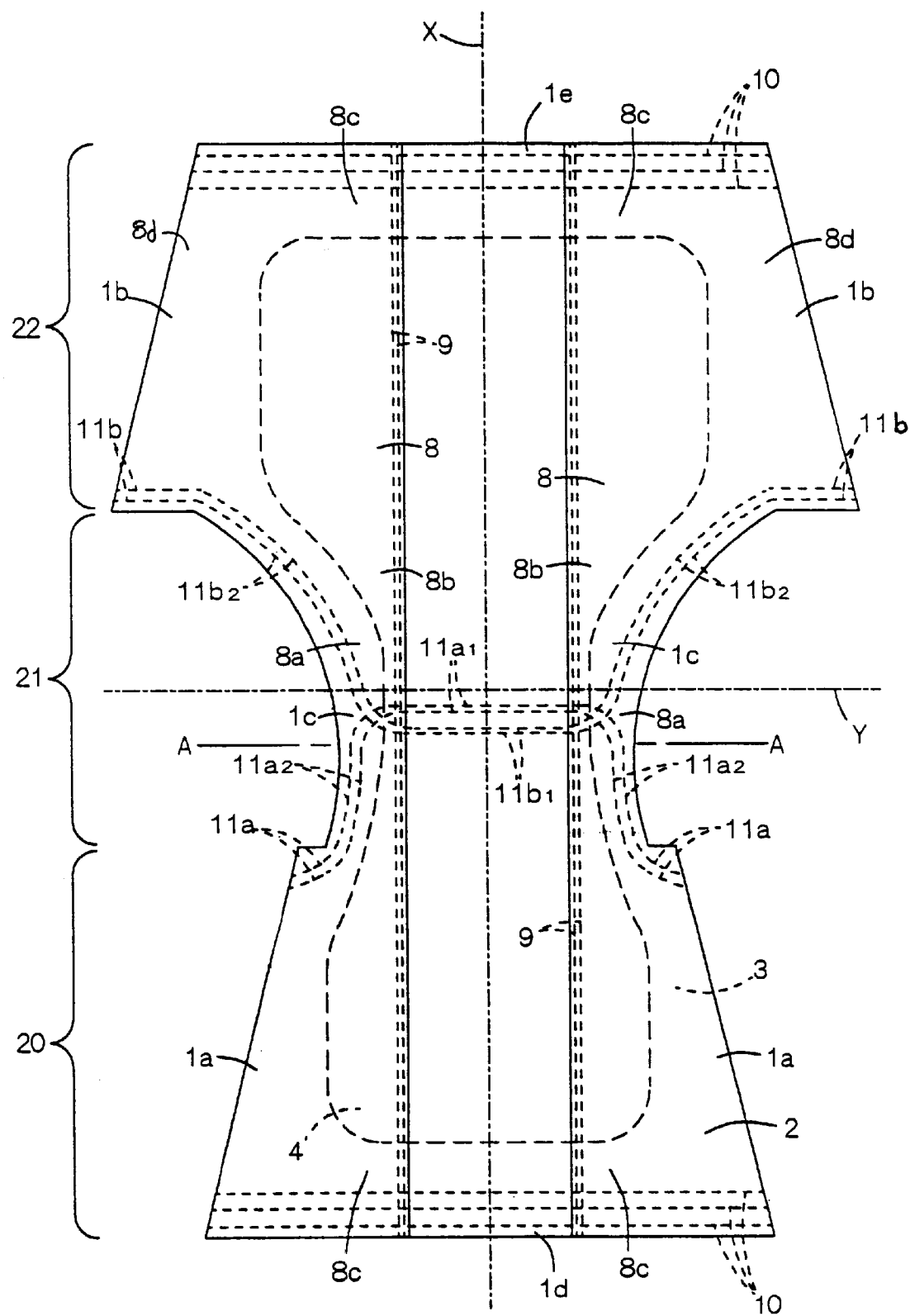
FIG. 2 is an exploded plan view showing the diaper of FIG. 1 before the side edge portions of the front and rear waist regions are bonded together.
Figure 3:
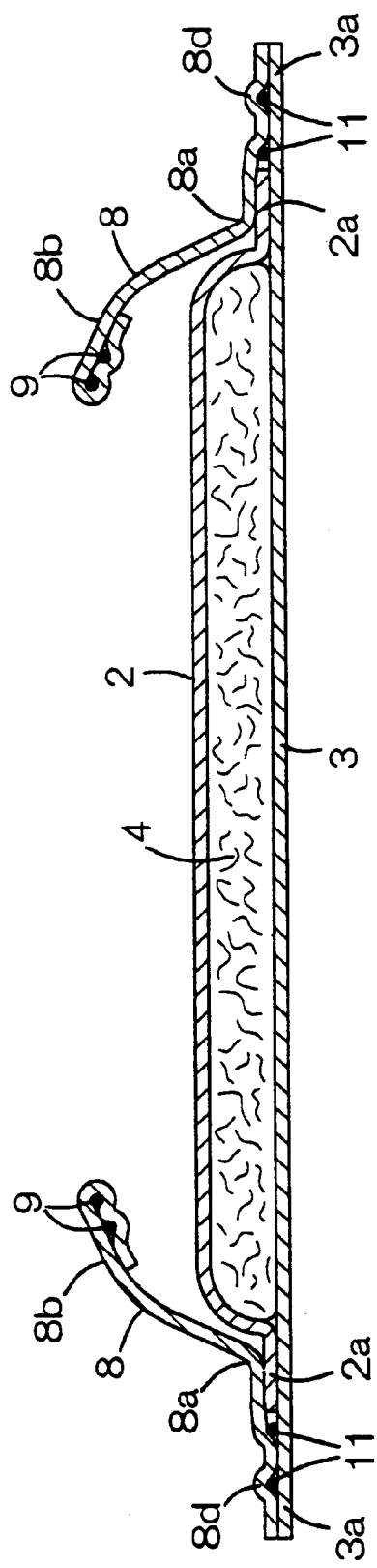
FIG. 3 is a sectional view taken along a line A—A in FIG. 2.

FIG. 1 is a perspective view showing a disposable pull-on diaper 1 as viewed from the side of a front waist region 20 and partially broken away, FIG. 2 is an exploded plan view of the diaper 1 shown in FIG. 1 before the side edge portions of the front and rear waist regions are bonded together and FIG. 3 is a sectional view taken along a line A—A in FIG. 2.

The diaper 1 basically comprises a liquid-pervious topsheet 2, a liquid-impervious backsheet 3 and a liquid-absorbent panel 4 disposed between the top- and backsheets 2, 3. The liquid-absorbent panel 4 has its entire surface covered with and bonded to liquid-pervious tissue paper (not shown) and is bonded to inner surface of at least one of the top- and backsheets 2, 3 via the tissue paper.

As seen in FIG. 2. the diaper 1 is longitudinally composed of a front waist region 20, a rear waist region 22 and a crotch region 21 extending between the front and rear waist regions 20, 22. The diaper 1 is contoured by transversely opposite side edge portions 1a, 1b, 1c extending in a longitudinal direction of the diaper 1 and longitudinally opposite end portions 1d, 1e extending in a transverse direction of the diaper 1. The side edge portions 1c in the crotch region 21 curve transversely inward so as to describe circular arcs. The side edge portions 1a, 1b, 1c are respectively, provided with leak-barrier cuffs 8 each extending in the longitudinal direction of the diaper 1.

In the diaper 1, the end portions 1d, 1e of the front and rear waist regions 20, 22, respectively, are dimensioned to be substantially equal to each other. The transversely opposite side edge portions 1c of the front waist region 20 extend from the end portion 1d toward the crotch region 21 so that these side edge portions 1a approach a longitudinal center line X bisecting a dimension defined between the transversely opposite edge portions 1a, 1b, 1c. In contrast, as the transversely opposite side edge portions 1b of the rear waist region 22 extend from the end portion 1e toward the crotch region 21, these side edge portions 1b depart from the longitudinal center line X.

To shape the diaper 1 from its state shown by FIG. 2 into a pull-on undergarment as shown in FIG. 1, the diaper 1 is folded with its inner surface inside along a transverse center line Y bisecting a dimension defined between the longitudinally opposite end portions 1c, 1d of the diaper 1. Then the transversely opposite side edge portions 1a, 1b of the front and rear waist regions 20, 22, respectively, are superimposed and bonded together. In the resulting pants-shaped diaper 1, a waist-hole 6 opens upward as shown in FIG. 1, a pair of leg-holes 7 open right- and leftward, respectively, also as shown in FIG. 1, respectively, and a pair of bonding zones 5 extend along the transversely opposite side edge portions 1a, 1b of the front and rear waist regions 20, 22.

Each of the bonding zones 5 comprises an upper end section 5a extending adjacent to the waist-hole 6 and a lower end section 5b extending adjacent to the associated leg-hole 7. The bonding zones 5 extend from the upper section 5a toward the lower end section 5b so that the bonding zones 5 approach and are oblique to the longitudinal center line X.

Two-dotted chain lines Z in FIG. 1 depict imaginary positions of the bonding zones 5 that have been translated toward the longitudinal center line X so as to intersect the longitudinal center line X. The angle θ at which the bonding zones extend with respect to the longitudinal center line X is preferably 5~30°.

With the diaper 1 put on a wearer's body, the upper end portions 5a of the respective bonding zones 5 lie at transversely lateral sides of the wearer and the lower end portions 5b of the respective bonding zones 5 lie on the belly of the wearer. Each of the bonding zones 5 comprises a plurality of heat-sealed lines 5c intermittently arranged in the longitudinal direction of the diaper 1.

Each of the cuffs 8 basically comprises a fixed side edge portion 8a fixed to the topsheet 2, a free side edge portion 8b opposed to the fixed side edge portion 8a and extending in the longitudinal direction, and longitudinal opposite end portions 8c collapsed inward transversely of the diaper 1 and bonded to the topsheet 2 in the collapsed state. In the rear waist region 22, the fixed side edge portion 8a further extends transversely outward to define an outer extension 8d. A longitudinally extending elastically stretchable member 9 is bonded under tension to the free side edge portion 8b of the cuff 8 in a manner that the elastically stretchable member 9 is wrapped by a part of the free side edge portion 8b. The cuff 8 is normally biased by the elastically stretchable member 9 to rise from the topsheet 2.

Elastic member 10 comprising a plurality of elastic elements which are circumferentially stretchable is bonded under tension to peripheral edge of the waist-hole 6. Portions of the elastic member 10 lying on the transversely opposite side edge portions 1a of the diaper 1 are disposed between the transversely opposite side edge portions 3a of the backsheet 3 and the outer extensions 8d of the respective cuffs 8 and bonded to at least one of these portions 3a, 8d. Remaining portions are disposed between the top- and backsheets 2, 3 and bonded to at least one of these sheets 2, 3.

An elastic member 11 comprising a plurality of elastic elements which are circumferentially stretchable is bonded under tension to each of the leg-holes 7 along the peripheral edge thereof. The elastic member 11 associated with the leg-hole 7 actually consists of a first elastic member 11a and a second elastic member 11b. These first and second elastic members 11a, 11b respectively have sections $11a_1$, $11b_1$ extending transversely across substantially middle zone of the crotch region 21, and sections $11a_2$, $11b_2$ extending along the transversely opposite side edge portions 1c of the diaper 1 in the crotch region 21. The respective sections $11a_1$, $11b_1$ of these first and second elastic members 11a, 11b are disposed between the backsheet 3 and the liquid-absorbent panel 4 and bonded to the backsheet 3 while the respective sections $11a_2$, $11b_2$ of these first and second elastic members 11a, 11b are disposed between and bonded to the transversely opposite side edge portions 3a of the backsheet 3 and the outer extension 8d of the cuff 8.

Referring to FIG. 1, as the respective elastic members 9, 10 and 11 contract, a plurality of gathers are formed along each of the peripheral edge of the waist-hole 6, the peripheral edges of the leg-holes 7 and the free side edge portions 8b of the cuffs 8, and the free side edge portions 8b rise from the topsheet 2.

Along the transversely opposite side edge portions 1a, 1b, 1c of the diaper 1, the transversely opposite side edge portions 2a of the topsheet 2 transversely extend outward slightly beyond the transversely opposite side edges of the liquid-absorbent panel 4 and the transversely opposite side edge portions 3a of the backsheet 3 as well as the outer extensions 8d of the cuffs 8 further extend transversely outward beyond the transversely opposite side edge portions 2a of the topsheet 2. The transversely opposite side edge portions 2a of the topsheet 2 are disposed between the transversely opposite side edge portions 3a of the backsheet 3 and the outer extensions 8d of the cuffs 8 and bonded to at least one of these. The side edge portions 3a of the backsheet 3 and the outer extensions 8d of cuffs 8 are superimposed and bonded together. Along the longitudinally opposite end portions 1d, 1e, portions of the top- and backsheets 2, 3 extending transversely outward beyond longitudinally opposite ends of the panel 4 are superimposed and bonded together.

Figure 4:
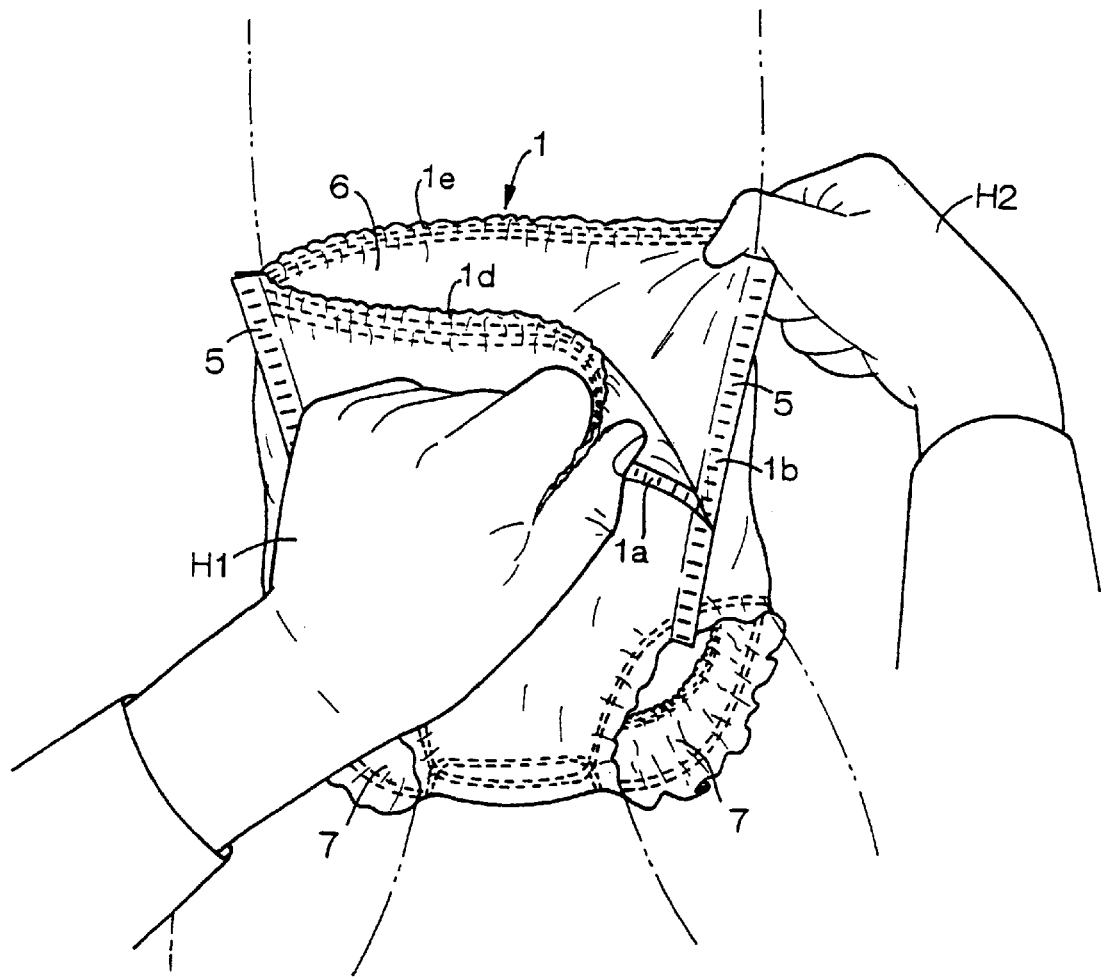
FIG. 4 is a diagram illustrating a manner in which the diaper is taken off from the wearer's body.

FIG. 4 illustrates a manner in which the diaper 1 is taken off from a wearer's body with the wearer lying on his or her back. As illustrated, the helper may grasp the end portion 1d of the diaper 1 with his or her left hand H1 and the end portion 1e of the diaper 1 with his or her right hand H2. To take the diaper 1 from the wearer's body, the side edge portions 1a and 1b may be torn open from the waist-hole 6 toward the leg-holes 7 by grasping and pulling the end portion 1d with the helper's left hand from the front waist region 20 toward the helper's own left flank while the end portion 1e in the rear waist region 22 is held by the helper's right hand. Then, with the end portion 1e held by the helper's left hand, the other side edge portions 1b and 1a may be torn open from the waist-hole 6 toward the leg-holes 7 by grasping and pulling the end portion 1d with the helper's right hand from the front waist region 20 toward the helper's own right flank.

The direction in which a force is exerted on the diaper 1 to tear it open is substantially coincident with the direction in which the respective bonding zones 5 extend. Consequently, the diaper 1 can be smoothly torn open along the respective bonding zones 5 without apprehension that the force might be exerted on any other zones than the bonding zones 5. According to this diaper 1, the angle θ at which the respective bonding zones 5 intersect the longitudinal center line X may be varied within a range of 5~30° to adjust alignment of the zones 5 with respect to the longitudinal center line X.

Figure 5:
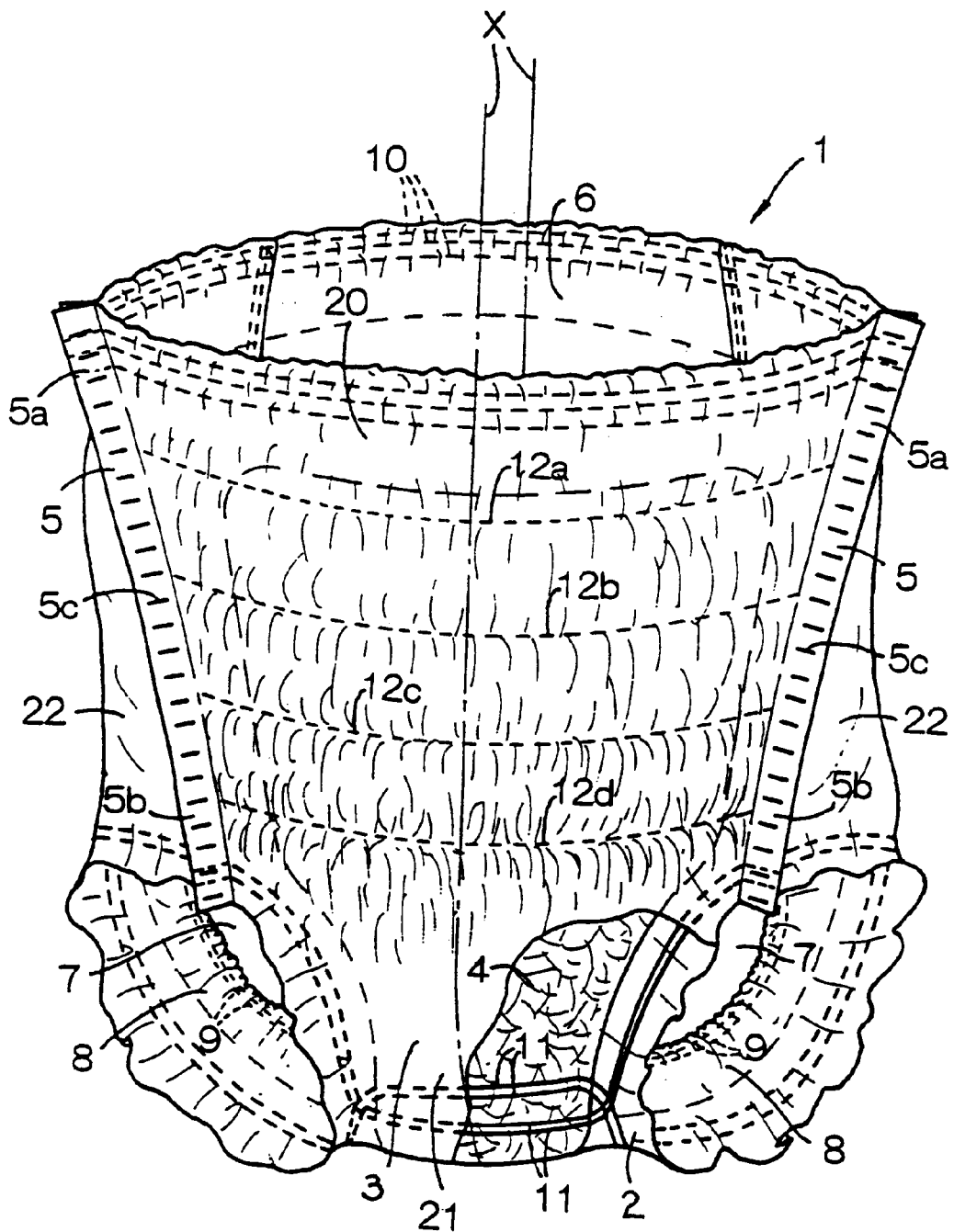
FIG. 5 is a view similar to FIG. 1 but showing another embodiment of the diaper.
Figure 6:
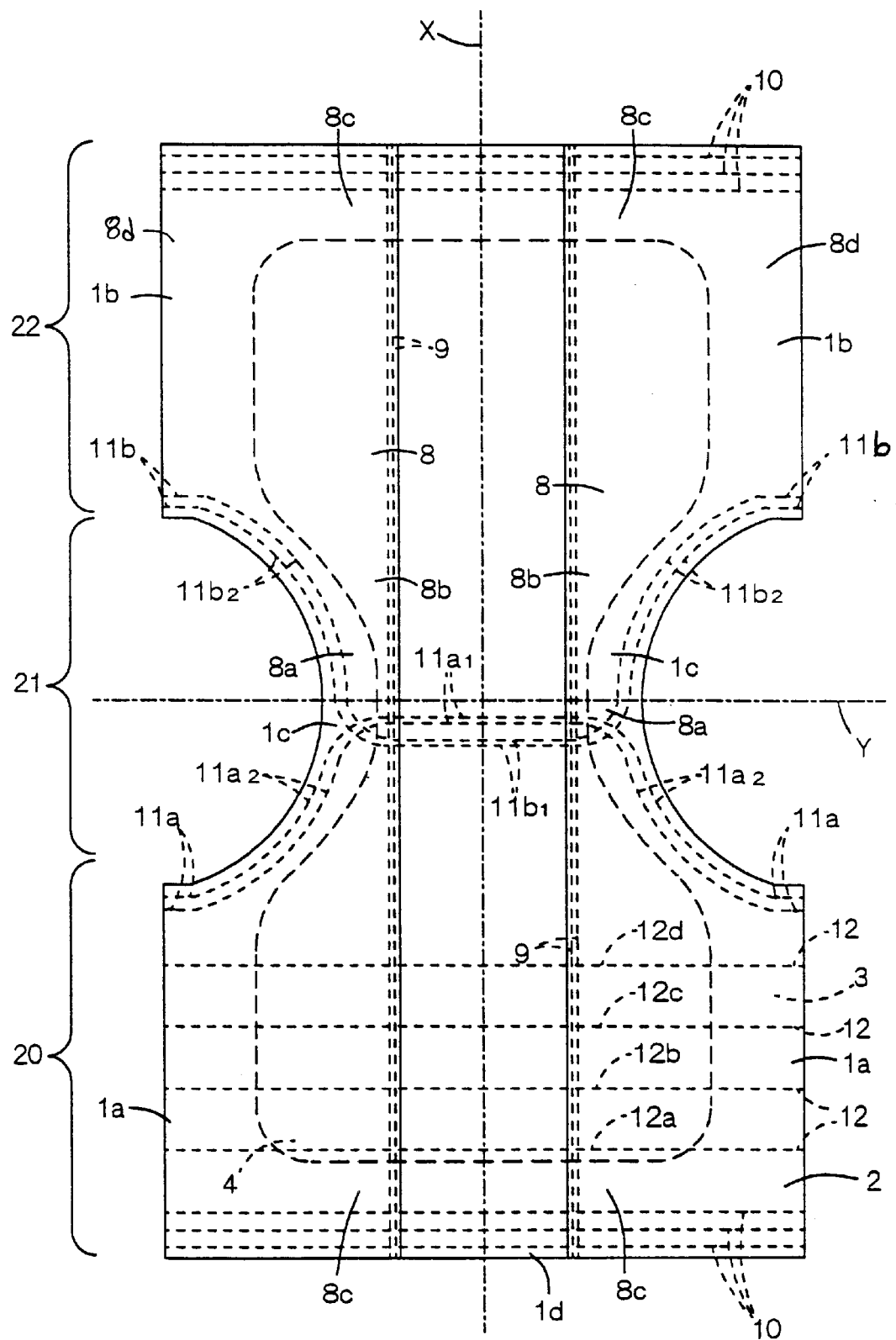
FIG. 6 is an exploded plan view showing the diaper of FIG. 5 before the side edge portions of the front and rear waist regions are bonded together.

FIG. 5 is a perspective view showing an alternative embodiment of the disposable diaper 1 according to this invention as viewed from the side of the front waist region 20 and FIG. 6 is an exploded plan view showing the diaper 1 of FIG. 5 before the side edge portions of the front and rear waist regions are bonded together. The diaper 1 of FIG. 5 basically comprises the similar elements to those constituting the diaper 1 of FIG. 1 and no detailed description of such similar elements is given hereunder.

According to this embodiment, the transversely opposite side edge portions 1a in the front waist region 20 as well as the transversely opposite side edge portions 1b in the rear waist regions 22 extend in parallel to each other and an auxiliary elastic member 12 comprising a plurality of elastic elements is bonded under tension to the diaper 1 so as to extend transversely across the front waist region 20 between the elastic member 10 associated with the waist-hole and the elastic members 11 associated with the respective leg-holes. The auxiliary elastic member 12 has its stretch stress gradually increasing from its element 12a lying most adjacent the elastic member 10 associated with the waist-hole toward its element 12d lying most adjacent the elastic members 11 associated with the leg-holes.

As will be apparent from FIG. 6, the waist-hole 6 opening upward as shown in FIG. 5 and the pair of leg-holes 7 opening left- and rightward also as shown in FIG. 5 are defined when the front and rear waist regions 20, 22 are bonded together along their transversely opposite side edge portions 1a, 1b of the front and rear waist regions 20, 22.

With the diaper 1 according to this embodiment, contraction of the respective elements 12a~12d constituting the auxiliary elastic member 12 causes an upper zone of the rear waist region 22 to be slightly drawn near toward the front waist region 20 and causes a lower zone of the rear waist region 22 to be drawn nearer to the front waist region 20 than the upper zone. The respective bonding zones 5 extend along the transversely opposite side edge portions 1a, 1b of the front and rear waist regions 20, 22 from upper ends 5a toward lower ends 5b thereof so that these bonding zones 5 approach the longitudinal center line X. With the diaper 1 put on the wearer's body, the upper ends 5a of the respective bonding zones 5 lie on transversely opposite flanks of the wearer and the lower ends 5b of the respective bonding zones 5 lie on the wearer's belly.

An alternative arrangement of the present invention is also possible in which the respective bonding zones 5 extend from the upper ends 5a toward the lower ends 5b approaching the longitudinal center line X so that the lower ends 5b lie on the wearer's hip. Such arrangement will be convenient when the diaper 1 is taken off from the wearer lying on his or her face.

The topsheet 2 may be formed from a liquid-pervious sheet such as a nonwoven fabric or a porous plastic film, and more preferably from a liquid-pervious and hydrophilic sheet. The backsheet 3 may be formed from a hydrophobic nonwoven fabric, a liquid-impervious plastic film or a laminated sheet consisting of a hydrophobic nonwoven fabric and a plastic film, and more preferably from a breathable and liquid-impervious sheet. It is also possible to form the backsheet 3 from a composite nonwoven fabric (SMS nonwoven fabric) comprising a highly water-resistant and flexible melt blown nonwoven fabric and two layers of spun bond nonwoven fabric positioned on surfaces of the melt blown nonwoven fabric.

The nonwoven fabric used for this invention may be of various types such as spun lace-, needle punch-, melt blown-, thermal bond-, spun bond-, chemical bond- and airthrough- types. The component fiber of the nonwoven fabric may be selected from a group including polyolefine-, polyester- and polyamide-based fibers and core-sheath-, eccentric core-sheath- and separated-type polyethylene/polypropylene or polyester conjugated fibers.

The elastic members 9, 10, 11, 12 may comprise a thread-, filament-, film- or ribbon-like elastomer of natural or synthetic rubber.

The panel 4 comprises a mixture of fluff pulp, high absorption polymer particles and thermoplastic synthetic resin fiber compressed to a desired thickness. The high absorption polymer may be selected from a group including graft polymers of starch-based, modified cellulose-based and synthetic polymers.

Bonding the top- and backsheets 2, 3 to each other or to the cuffs 8, bonding of the panel 4 and attaching of the elastic members 9, 10, 11 may be carried out by means of suitable adhesive such as a hot melt adhesive or a pressure-sensitive adhesive, or using suitable welding technique such as heat sealing or supersonic sealing technique. Use of the hot melt adhesive is particularly preferable as the adhesive means.

This invention is not limited to the disposable pull-on diaper but applicable also to other disposable pull-on undergarments such as training pants or incontinent pants.

In the disposable pull-on undergarment according to this invention, the respective bonding zones extend from the upper ends toward the lower ends thereof, getting nearer to the longitudinal center line so that the lower ends may lie on the wearer's belly or hip. When the diaper is taken off from the wearer lying on his or her back or on his or her face, the direction in which the force is exerted on the diaper to tear it open is substantially coincident with the direction in which each of the bonding zones extend and therefore, substantially no force is exerted on any other zones than the bonding zones. As a result, the diaper can be smoothly torn open along the respective bonding zones.

What is claimed is:

1. A disposable pull-on undergarment comprising:
   front and rear waist regions having transversely opposite side edge portions, said front and rear waist regions being opposed to each other;
   a crotch region extending between said front and rear waist regions;
   said transversely opposite side edge portions of said front and rear waist regions being bonded together along bonding lines that extend along said transversely opposite side edge portions of said front and rear waist regions;
   a waist-hole; and
   a pair of leg-holes;
   said bonding lines having upper end portions lying adjacent said waist-hole and lower end portions lying adjacent said pair of leg-holes;
   said bonding lines being aligned so that they approach a longitudinal center line vertically extending across circumferential middle zones of said front and rear waist regions as they extend from said upper end portions toward said lower end portions thereof;
   said transversely opposite side edge portions of said front and rear waist regions coinciding and being aligned with said bonding lines.

2. The disposable pull-on undergarment according to claim 1, wherein said bonding lines extend at an angle of 5° to 30° with respect to said longitudinal center line.

3. The disposable pull-on undergarment according to claim 1, further comprising:
   a liquid-previous topsheet;
   a liquid-impervious backsheet; and
   a liquid-absorbent panel disposed between said liquid-previous topsheet and said liquid-impervious backsheet.

* * * * *